US00PP18081P2

(12) United States Plant Patent
Hanes

(10) Patent No.: US PP18,081 P2
(45) Date of Patent: Sep. 25, 2007

(54) ***PELARGONIUM* PLANT NAMED 'CANTE LAVER'**

(50) Latin Name: *Pelargonium×hortorum×Pelargonium torgaense hybrid*
Varietal Denomination: Cante Laver

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/369,525

(22) Filed: Mar. 7, 2006

(51) Int. Cl.
*A01H 5/00* (2006.01)

(52) U.S. Cl. ..... Plt./329
(58) Field of Classification Search ..... Plt./329
See application file for complete search history.

*Primary Examiner*—Anne Marie Grunberg
*Assistant Examiner*—Georgia Helmer
(74) *Attorney, Agent, or Firm*—Jondle & Associates, P.C.

(57) ABSTRACT

A *pelargonium* cultivar particularly distinguished by single-type lavender flowers with white eyes, medium to large umbrella-shaped inflorescences, medium-green to grass-green foliage with very weak zonation, a compact to medium-sized with a spreading, prostrate to semi-trailing plant habit, a very well-branched and dense plant habit, and an early to mid-season flowering response, is disclosed.

2 Drawing Sheets

Genus and species: *Pelargonium×hortorum×Pelargonium tongaense* hybrid.
Variety denomination: 'Cante Laver'.

BACKGROUND OF THE NEW PLANT

The present invention comprises a new and distinct cultivar of *pelargonium,* botanically known as *Pelargonium×hortorum×Pelargonium tongaense* hybrid, and herein after referred to by the cultivar name 'Cante Laver'. The new cultivar was a product of a planned breeding program which had the objective of creating new varieties having various colors and a moderately compact and well-branched plant habit. The female parent was the proprietary dark red-flowered '8961-2' (unpatented) *pelargonium,* and the male parent was the proprietary dark red-flowered '9104-1' (unpatented) *pelargonium.* The hybridization occurred in October 2001 and the resulting seeds were sown in a greenhouse in February 2002. A single plant selection was chosen for further evaluation and for asexual propagation in the Summer of 2003, in Gilroy, Calif.

The new cultivar was created in 2001 in Gilroy, Calif. and has been asexually reproduced repeatedly by vegetative cuttings and tissue culture in Gilroy, Calif. over a two-year period. 'Cante Laver' has not been observed under all possible environmental conditions. 'Cante Laver' has also been trialed at Gilroy, Calif. and Hillscheid, Germany. 'Cante Laver' has been found to retain its distinctive characteristics through successive asexual propagations.

Plant Breeder's Rights for this cultivar were applied for in Canada on Mar. 29, 2005, and with the European Union on Sep. 20, 2005.

SUMMARY OF THE INVENTION

The following are the most outstanding and distinguishing characteristics of the new cultivar when grown under normal commercial practices in Hillscheid, Germany.

1. Single-type lavender flowers with white eyes;
2. A medium to large, umbrella-shaped inflorescence;

3. Medium-green to grass-green foliage with very weak zonation;
4. A medium-sized and compact plant habit;
5. A compact to medium-sized, with a spreading to prostrate to semi-trailing plant habit;
6. A well-branched and dense plant habit; and
7. An early to mid-season flowering response.

DESCRIPTION OF THE PHOTOGRAPHS

This new geranium plant is illustrated by the accompanying photographs which show the overall plant habit, including inflorescences, buds, and foliage of the plant; the colors shown are as true as can be reasonably obtained by conventional photographic procedures. The photographs are of a 22-week-old plant grown from outdoors from rooted cuttings in the mid-Summer under conditions which approximate those generally used in commercial practice.

DESCRIPTION OF THE NEW CULTIVAR

Figure 1:
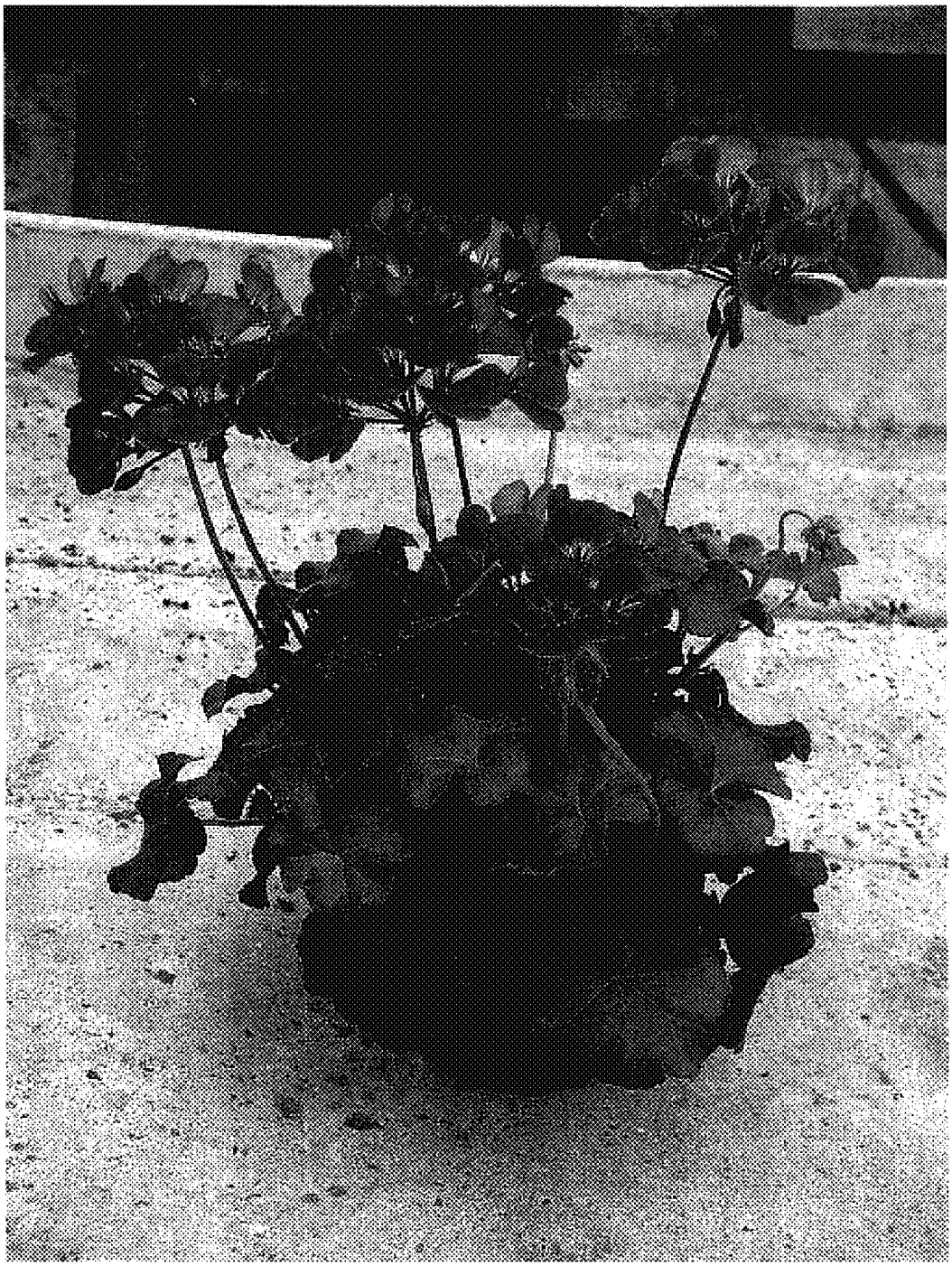
FIG. 1 shows the overall plant habit, including inflorescences, buds and foliage of the plant.
Figure 2:
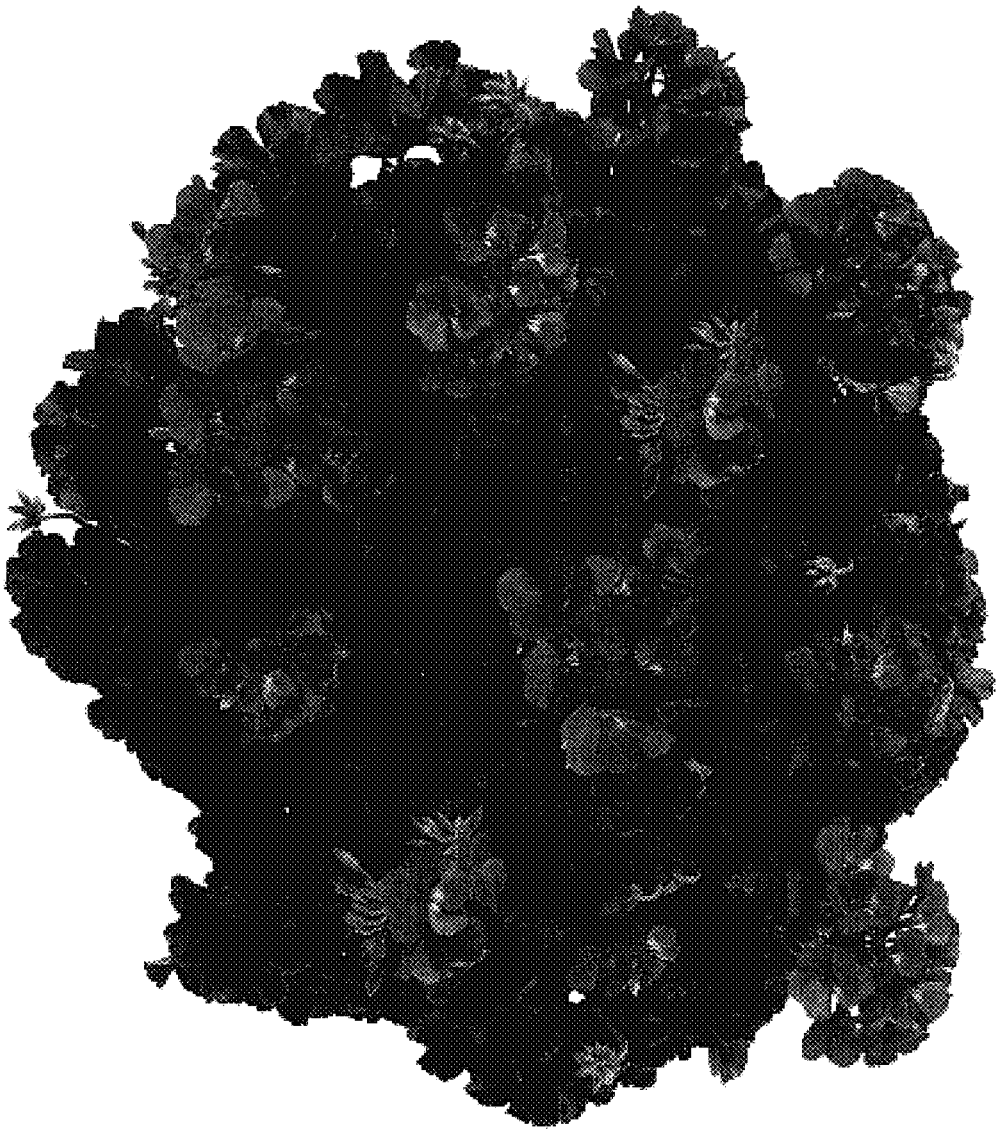
FIG. 2 shows a view from above of a 45-cm diameter tub holding 3 flowering plants.

The following detailed descriptions set forth the distinctive characteristics of 'Cante Laver'. The data which defines these characteristics were collected from asexual reproductions carried out in Hillscheid, Germany. The plant history was taken on un-pinched, 13-week-old plants grown in 12-cm pots in a greenhouse in late May 2005. The color readings were taken under natural light in the greenhouse in May 2005. Color references are primarily to The R.H.S. Colour Chart of The Royal Horticultural Society of London (R.H.S.) (2001).

DETAILED BOTANICAL DESCRIPTION

Classification:
*Botanical.*—*Pelargonium×hortorum×Pelargonium tongaense* hybrid.
*Common name.*—Hybrid geranium.

Parentage:

*Female parent.*—'8961-2', a proprietary (unpatented) dark red-flowered *pelargonium.*

*Male parent.*—'9104-1', a proprietary (unpatented) dark red-flowered *pelargonium.*

Plant:

*Form.*—Shrub; self-branching, free and strong branching, low mounding and prostrate to partly overhanging dense plant habit with short internodes.

*Branching habit.*—15 to 20 branches per plant.

*Height* (*as measured from the soil surface to the surface of the foliage canopy, excluding the inflorescence*) .—11.7 cm for a 13-week-old plant.

*Width* (*horizontal diameter*).—29.3 cm.

*Time to produce a finished flowering plant.*—11 to 12 weeks for a 12 cm to 14 cm pot.

*Outdoor plant performance.*—Use in containers, hanging baskets, and as bedding plants.

*Time to initiate and develop roots.*—24 days.

*Root description.*—Fibrous.

Leaves:

*Arrangement.*—Alternate, partly appearing opposite at flowering branches.

*Shape.*—Kidney-shaped with moderate lobes with the gap between the lowest lobes often closed; distinctly wavy.

*Immature leaf.*—Color: General: Grass-green. Upper surface: RHS 137D to RHS 143A. Lower surface: RHS 143B.

*Mature leaf.*—Color: Upper surface: RHS 137C (light medium-green). Lower surface: RHS 137D. Length: 8.7 cm. Width: 5.0 cm.

*Zonation.*—Color: RHS 147A (olive-green) with a very weak distinctness. Size: The ring is about 3.0 cm in diameter, while the belt of the zonation is 1.0 cm wide.

*Apex.*—Rounded.

*Base.*—Cordate with the gap between the lowest lobes mostly closed or slightly overlapping.

*Margin.*—Crenate.

*Texture.*—Upper surface is smooth; although the leaves appear like those of ivy geraniums, they are softer and not leathery.

Petioles:

*Length.*—5.5 cm.

*Diameter.*—0.2 cm.

*Color.*—RHS 143C (light-green).

*Texture.*—With short pubescence.

Stems:

*Length.*—10 cm to 13 cm.

*Internode length.*—0.5 cm to 1.5 cm.

*Diameter* (*at the midpoint*).—0.4 cm to 0.5 cm.

*Color.*—Mainly RHS 143C (light-green).

*Texture.*—With very short pubescence.

Inflorescence buds:

*Length* (*just before the petals unfold*).—2.1 cm.

*Diameter* (*just before the petals unfold*).—1.0 cm.

*Shape.*—Narrow and elliptical.

*Sepal color* (*just before the petals unfold*).—RHS 143A (green).

*Petal color* (*just before the petals unfold*).—RHS 67B (purple-pink).

Inflorescence:

*Type.*—An umbel composed of about 25 flowers and buds.

*Average number of open inflorescences per plant.*—7.

*Number of inflorescences per plant in early September.*—15 to 20.

*Blooming habit.*—Flowers continuously during the Summer.

*Umbel diameter.*—10.8 cm.

*Umbel depth* (*height*).—5.0 cm.

*Umbel shape.*—Umbrella-shaped and moderately tight.

*Lastingness of the umbel on the plant.*—15 to 18 days.

*Peduncle.*—Length: 17.8 cm. Diameter: 0.3 cm. Texture: Very fine and short pubescence but appears smooth. Color: RHS 143C (light-green).

*Pedicel.*—Length: 4.7 cm. Diameter: 0.1 cm, with a spur near the base. Texture: Weakly pubescent. Color: RHS 183A (deep purple-brown).

Corolla:

*Form.*—Single-type, zygomorphic.

*Shape.*—Cup-shaped with a gap between the upper and lower petals.

*Number of petals.*—5.

*Petaloids.*—Present as thread-like or strap-like stamens that are white to light-violet.

*Size.*—Width: 4.7 cm.

*Lastingness of the individual flowers on the plant.*—5 to 7 days at 18° C.

*Fragrance.*—None.

Petals:

*Upper petals.*—Length: 2.0 cm to 2.2 cm. Width: 1.6 cm to 1.8 cm. Color: Upper surface: RHS N74B. Lower surface: RHS 72D.

*Markings.*—White base and RHS 67A (bluish-pink) fine veins.

*Lower petals.*—Length: 2.3 cm. Width: 1.8 cm to 2.0 cm. Color: Upper surface: RHS 74B. Lower surface: RHS 72D. Markings: None.

*Shape.*—Obovate.

*Apex.*—Rounded.

*Base.*—Acute or attenuate.

*Margin.*—Entire.

*Texture.*—Smooth.

Sepals:

*Number.*—5.

*Length.*—Approximately 1.0 cm.

*Width.*—0.4 cm for the largest upper sepal and 0.3 cm for the other sepals.

*Shape.*—Ensiform.

*Apex.*—Acute.

*Base.*—Fused.

*Margin.*—Entire.

*Texture.*—Finely pubescent.

*Color.*—Mainly RHS 143C (light-green) for both upper and lower surfaces; RHS 179A (reddish-brown) at the base of the largest sepal; RHS 180B for both the outer and inner surfaces.

Reproductive organs:

*Androecium.*—Number of anthers: 5 to 7. Filament color: RHS 155D (white). Filament length: 0.6 cm. Pollen color: RHS 26A (yellow-orange). Pollen amount: Moderate.

*Gynoecium.*—Number of pistils: 1. Pistil length: 0.9 cm. Stigma color: RHS 73B (bluish-pink). Stigma shape: 5 to 6-lobed. Style color: RHS 73B. Style length: 0.3 cm. Style shape: Filiform (filament-like) with the lobes of the stigma at right angles.

Fruit/seed set: Occasionally a few seeds in the Summer and relatively more in the late Summer to Fall, are developed, where the total length of the fruit is 3.8 cm, the ovary is oval with a long beak; up to five seed grains with spiral-shaped attachments are set free. Some of these seed will be fertile seeds, but not very many.

Disease and insect resistance: Average/typical for the species; no special observations made.

COMPARISON WITH PARENTAL AND COMMERCIAL CULTIVARS

'Cante Laver' differs from the female parent '8961-2' (unpatented) in that 'Cante Laver' has lavender flowers, while '8961-2' has dark red flowers. Additionally, 'Cante Laver' has shorter peduncles and a stronger basal branching plant habit than '8961-2'.

'Cante Laver' differs from the male parent '9104-1' (unpatented) in that 'Cante Laver' has lavender flowers, while '9104-1' has dark red flowers. Additionally, 'Cante Laver' has lighter green foliage and a more prostrate and less upright plant habit than '9104-1'.

'Cante Laver' differs from the commercial variety 'Cante Ros' (U.S. Plant Pat. No. 15,843) in that 'Cante Laver' has lavender flowers, while 'Cante Ros' has pink flowers. Additionally, 'Cante Laver' has larger inflorescences and a more compact plant habit than 'Cante Ros'.

I claim:

1. A new and distinct cultivar of *pelargonium* plant as shown and described herein.

* * * * *